United States Patent [19]

Scanlon

[11] Patent Number: 5,085,983
[45] Date of Patent: Feb. 4, 1992

[54] DETECTION OF HUMAN TUMOR PROGRESSION AND DRUG RESISTANCE

[75] Inventor: Kevin J. Scanlon, Pasadena, Calif.

[73] Assignee: City of Hope, Duarte, Calif.

[21] Appl. No.: 352,994

[22] Filed: May 17, 1989

Related U.S. Application Data

[63] Continuation-in-part of Ser. No. 234,096, Aug. 19, 1988, which is a continuation-in-part of Ser. No. 46,127, May 5, 1987, abandoned.

[51] Int. Cl.$^5$ .......................... C12Q 1/68; C12P 19/34; G01N 33/566; C07H 15/12
[52] U.S. Cl. .......................................... 435/6; 435/91; 436/501; 436/94; 536/26; 536/27; 536/28; 536/29; 935/77; 935/78
[58] Field of Search .................. 435/6.91; 436/501, 94; 536/26, 27; 935/77, 78

[56] References Cited

U.S. PATENT DOCUMENTS 4,683,195 7/1987 Mullis et al. .......................... 536/27
4,699,877 10/1987 Cline et al. ............................ 436/503

OTHER PUBLICATIONS

Brisson et al., Gene 28:271-275 (1984).
Farr et al., PNAS(USA) 85:1629-1633 (Mar. 1988).
Kagimoto et al., Int. J. Cancer 35: 809-812 (1985).
Kashani-Sabet et al., Canc. res. 48(20): 5775-5778 (Oct. 15, 1988).
Kraker et al., Cancer Lett. (Ireland) 38(3): 307-314 (1988).
Lu et al., J. Biol Chem. 263(10): 4891-4894 (Apr. 4, 1988).
Sengupta et al., Biochem. Biophys Res. Comm. 136(1):341-347 (Apr. 14, 1986).
Scanlon et al., PNAS(USA)85: 650-653 (Feb. 1988).
Takeishi et al., Nuc. Acids Res. 13(6):2035-2042 (1985).
Van Stratten et al., PNAS(USA)80:3183-3187 (Jun. 1983).
Verlaan-de Vries et al., Gene 50:313-320 (1986).
Watt et al., Nature (Lond) 303:725-728 (1983).

Primary Examiner—Robert A. Wax
Assistant Examiner—Stephanie W. Zitomer
Attorney, Agent, or Firm—Edward S. Irons

[57] ABSTRACT

Changes in tumor cell RNA and DNA are utilized to detect the progression and the temporal changes in resistance to chemotherapy in human tumors.

28 Claims, 13 Drawing Sheets

Analysis of DNA from colon cells sensitive and resistant to cisplatin

DNA analysis of human ovarian tissue for DNA polymerase $\beta$

Eco RI

DNA analysis of human leukemic cells for DNA polymerase $\beta$

Southern

K562  CEM  ANLL
S  DDP  araC   S  VP16  MTX

Kb
-21.8
-ABOUT 15Kb
- 9.6
- 6.6
- 5.2
- 4.3

Eco RI

DNA analysis of DNA polymerase α in normal and colon carcinoma tissue

DETECTION OF HUMAN TUMOR PROGRESSION AND DRUG RESISTANCE

This application is a continuation-in-part of copending application Ser. No. 234,096 filed Aug. 19, 1988 as a continuation-in-part of application Ser. No. 046,127 filed May 5, 1987 and abandoned Dec. 5, 1988.

BACKGROUND OF THE INVENTION

The efficiency of cancer chemotherapy protocols tends progressively to decrease in inverse proportion to the target tumor's progressive increase in drug resistance. Accordingly, early detection of drug resistance would significantly benefit the development, choice and timing of alternative treatment strategies. Currently, the multidrug resistant (MDR) gene offers a potential for monitoring tumor resistance to some natural agents such as the vinca alkaloids, Vincristine and Vinblastine; antibiotics such as Daunorubicin, Actinomycin D, Doxorubicin, Mitomycin C, Etoposide (VP-16), Teniposide (VM-26) and Mithramycin.

Amplification of genes associated with drug resistance has been monitored by a modified polymerase chain reaction (PCR) assay, as described in Kashani-Sabet, et al., "Detection of Drug Resistance in Human Tumors by in Vitro Enzymatic Amplification," Cancer Res. 48:5775–5778 (1988). Acquired drug resistance has been monitored by the detection of cytogenetic abnormalities, such as homogeneous chromosome staining regions and double minute chromosomes.

Several shortcomings attend these procedures. Gene amplification techniques other than PCR are applicable only to DNA, require at least $10^6$ tumor cells and cannot discriminate less than two to four fold changes, whereas drug resistant tumors may be indicated by lower gene amplification levels. Drug resistance has been manifested by tumors in the absence of gene amplification or cytogenetic abnormalities. The detection of tumor progression by imaging lacks reliability and precision.

No efficient, generally applicable non-invasive procedure for the early detection of or for monitoring the changes in drug resistance over time is presently known.

SUMMARY OF THE INVENTION

This invention utilizes changes in tumor cell RNA and DNA to detect the progression and the temporal changes in resistance to chemotherapy of human tumors. Such changes are evidenced, for example, by qualitative and quantitative differences in RNA and DNA and by the differences and degree of differences between the Southern analysis patterns of DNA from specific cancer cell genes.

The invention also includes the identification of human cancer marker genes characterized by unique gene transcript DNA patterns and pattern changes revealed, for example, by Southern analysis as cells pass progressively from a normal to a cancerous or drug resistant state. Procedures for the clinical monitoring of tumor progression and of the beginning and progression of drug resistance by comparison of DNA patterns of sequential tumor gene transcripts are described.

DESCRIPTION OF THE PCR ASSAY

FIG. 1 is a schematic diagram outlining the steps of a modified PCR assay useful in the invention. Two converging, preferably about 15 to 25 base, oligoprimers oriented in opposite directions, are provided for the 5' and 3' ends of the gene sequence to be analyzed. See Kashani-Sabet, et al., supra.

Tumor cells for the PCR assay are obtained from patients' tissue or peritoneal fluid, and total RNA for use as a template is isolated.

To replicate a specific sequence which preferably includes a restriction site, the oppositely oriented primers are annealed to the RNA template. Addition of reverse transcriptase yields first strand polymerization. Cycles of denaturation, annealing, and polymerization ensue upon addition of heat-stable DNA Polymerase. This process is continued for a plurality of rounds. Inclusion of ribonuclease A after the completion of round one tends to eliminate RNA which may compete for primer binding.

In general, the amplified sequence, or a restriction fragment thereof, is detected in the reaction product by hybridization with a complementary probe. The amplified DNA is cut with a restriction enzyme. The resulting fragments are separated by gel electrophoresis. The gel is then laid on a piece of nitrocellulose, and a flow of an appropriate buffer is set up through the gel, perpendicular to the direction of electrophoresis, toward the nitrocellulose filter. The flow causes the DNA fragments to be carried out of the gel onto the filter, where they bind, so that the distribution of the DNA fragments in the gel is replicated on the nitrocellulose. The DNA is then denatured and fixed onto the filter. A complementary radioactively labeled probe is then hybridized to the DNA sequence on the filter. Autoradiography of the filter identifies which fragment or fragments contain the sequence under study, each fragment being identified according to its molecular weight. A variation on this technique is to hybridize and do autoradiography directly in the gel, rather than on a nitrocellulose filter.

Table I identifies target and primer sequences and restriction sites for eleven gene transcripts.

TABLE I

Oligonucleotide Primers of RNA Expression in Drug Resistant Tumor Cells

| Transcript | Amplified Fragment Predicted Size (bp) | Restriction Site | Location of the Oligonucleotide in the Nucleotide Sequence* | | Probe |
| --- | --- | --- | --- | --- | --- |
| | | | Primers | | |
| | | | 5'oligo nucleotide | 3'oligo nucleotide | |
| DHFR | 136 | Ava II | 1301–1321 | 1406–1386 | 1364–1340 |
| dTMP synthase | 171 | Pst I | −3–21 | 168–146 | 122–101 |
| T kinase | 184 | Hinf I | 58–83 | 242–219 | 141–119 |
| DNA pol α | 202 | Hae III | 138–158 | 340–318 | 240–215 |
| DNA pol β | 108 | Kpn I | 21–46 | 129–103 | 98–73 |
| c-fos | 121 | Pst I | 908–927 | 1029–1010 | 985–961 |
| c-myc | 300 | Alu I | 1–24 | 300–277 | 216–193 |

TABLE I-continued

Oligonucleotide Primers of RNA Expression in Drug Resistant Tumor Cells

| Transcript | Amplified Fragment | | Location of the Oligonucleotide in the Nucleotide Sequence* | | |
|---|---|---|---|---|---|
| | Predicted Size (bp) | Restriction Site | 5'oligo nucleotide | 3'oligo nucleotide | Probe |
| H-ras | 273 | Msp I | 1661–1680 | 2183–2202 | 1782–1763 |
| Multidrug Resistant (MDR) I | 332 | Hph I | 16–39 | 342–321 | 201–180 |
| β Actin | 240 | Bgl II | 25–44 | 269–245 | 155–132 |
| Phosphglycerate Kinase (PGK) | 166 | Alu I | 1364–1386 | 1529–1507 | 1405–1427 |

*See Journal of Clinical Laboratory Analysis, Vol. 3, No. 5 (August 1989) (In Press).

FIGS. 2–7 are schematic maps which identify the target, primer and probe sequences and the position of the primers for use in PCR assays of the DHFR, dTMP, DNA polymerase β, c-fos, c-myc, and H-ras genes. Optimum amplification requires selection of appropriate primers for each selected gene sequence.

As shown in FIG. 2, DHFR-3 (#3) is the 3'-5' oligoprimer complementary to DNA (bases 1301–1321) having the sequence CGG AGG TCC TCC CGC TGC TGT. #2 is the 5'-3' oligoprimer complementary to mRNA (bases 1386–1406) having the sequence GAG CGG TGG CCA GGG CAG GTC. The target sequence bases 1301–1406 includes an Ava 2 restriction site. The probe for identifying the target sequence has the sequence GTT CTG GGA CAC AGC GAC GAT GCA.

Oligoprimers and probes for the dTMP synthase gene are shown in FIG. 3. The target sequence includes bases −3 to 168. #2 is the 3'-5' oligoprimer complementary to DNA (bases −3 to 21) having the sequence GCC ATG CCT GTG GGC CGG CCT TCC CCG GAG. #3 is the 5'-3' primer complementary to mRNA (bases 146–168) having the sequence AGG GTG CCG GGG TTG CCC GTG CGGT. #4 (bases 101 to 122) is the probe for identifying the target sequence. The probe has the sequence AGG ATG TGT TGT GGA TCT GCC CA. The target sequence includes a PstI restriction site.

Oligoprimers and probes for the DNA polymerase β gene are shown in FIG. 4. #1 is the 5'-3' oligoprimer complementary to DNA (exon 1, bases 21–46) having a sequence of GGA GCT GGG TTG CTC CTG CTC CCG T. #2 is the 5'-340 oligoprimer complementary to m-RNA (exon 1 bases 103–129) having a sequence GCC TTC CGT TTG CTC ATG GCG GCC T. #3 is the probe (bases 73–98) for identifying the target sequence bases 21 to 129. The probe sequence is ACC AGG GAC TAG AGC CCT CTC CCA G. The target sequence includes a KpnI restriction site.

Oligoprimers and probes for the c-fos gene are shown in FIG. 5 #1 is the 5'-3' oligoprimer complementary to m-RNA (exon 1, bases 908–927) having a sequence ACG CAG ACT ACG AGG CGT CA. #2 is the 5'-3' oligoprimer complementary to DNA (exon 1, bases 1010–1029) having a sequence CTG CGC GTT GAC AGG CGA GC. The target sequence includes bases 908 to 1029. #4 is the probe for identifying the target sequence (bases 961–985) has the sequence TGA GTG GTA GTA AGA GAG GCT ATC. The target sequence includes a Pst I restriction site.

Oligoprimers and probes for the c-myc gene are shown in FIG. 6. #1 is a 5'-3'0 oligoprimer complementary to either DNA or RNA (exon 1, bases 1–24) having a sequence of TCC AGC TTG TAC CTG CAG GAT CTG. #2 is the 5'-3' oligoprimer complementary to DNA or a probe for RNA (exon 2, bases 193–216). It has a sequence GAC CAC CGA GGG GTC GAT GCA CTC T. #3 is a 5'-3' oligoprimer complementary to only RNA (exon 2, 277–300) having the sequence AGG AGC CTG CCT CTT TTC CAC AGA. There is a base 87 AluI restriction site between 1 and 300. The target sequence, bases 1–300 includes an Alu I restriction site at base 87.

Oligoprimers and probes for the H-ras gene are shown in FIG. 7. The amplified fragment stretches from base 1661 to base 2202 (541 DNA bases, 273 RNA bases). #1, a sense oligonucleotide, spans bases 1661–1680 and contains the sequence: 5'-TGAG-GAGCGATGACGGAATA-3'. #2 is an antisense oligonculeotide, encodes nucleotides 2183 to 2202 and has the sequence: 5'-GACTTGGTGTTGTT-GATGGC-3'. #3 is the probe oligonucleotide spanning bases 1763-1782 and encodes the sequence: 5'-ACCTCTATAGTAGGGTCGTA-3'. #1 and #2 are used as primers for the polymerization assay. #3 is used as the probe to detect the amplified target sequence. The 273 base RNA sequence contains a cleavage site for MspI at position 1786 which yields two fragments of 136 and 137 base pairs in length upon digestion. Only the 171 base pair cleavage fragment contains the sequence complementary to #3. Hybridization of the digested PCR product with the end labeled probe should yield only one band.

Table II relates some of the several genes useful in this invention to chemotherapeutic agents.

TABLE II

| Gene | Cancer Chemotherapeutic Agents |
|---|---|
| TS Cycle | |
| DHFR | Methotrexate (MTX) |
| dTMP Synthase | Cisplatin, 5FUra, FdUrd |
| Thymidine Kinase | Cisplatin, MTX, 5FUra, FdUrd |
| DNA Repair Enzymes | |
| DNA polymerase α | Cisplatin |
| DNA polymerase β | Cisplatin, araC, alkylating agents, some natural products, and X-ray Radiation |
| Oncogenes | |
| c-fos | Cisplatin |
| c-myc | Cisplatin, MTX, araC, VP-16 |
| H-ras | Cisplatin |
| Multidrug Resistance Genes | |
| MDR I | Adriamycin, Actinomycin D |
| Topoisomerase II | colchicine, Vinblastine, Vincristine, daunorubicin, VP-16, VM-26 and mithramycin |
| Glutathione-S Transferase (GST) | Alkylating agents |

DESCRIPTION OF PREFERRED EMBODIMENTS

The preferred embodiments of the invention utilize the DNA polymerase α and β genes, the dTMP gene, the DHFR gene, the MDR gene and the c-fos, c-myc and H-ras oncogenes.

The DNA polymerase β gene has been shown to be elevated in drug resistant tumor cells treated with antimetabolites, e.g., ara-C, alkylating agents, some natural products, e.g., VP-16, and cisplatin. Changes in the DNA of DNA polymerase β evidence the progression of tumor formation and temporal changes in drug resistance.

Most chemotherapeutic agents damage DNA directly or indirectly. The dTMP synthase cycle is the sole de novo source of thymidine, the availability of which is rate limiting in DNA synthesis and the repair of DNA damage. The dTMP cycle accordingly has been a selected target for several cancer therapeutic agents, such as methotrexate (MTX), 5-fluorouracil (5-FUra) and fluorodeoxyuridine (FdUrd).[1] Tumor cells resistant to cisplatin display increased levels of dTMP synthase by elevated gene expression in vitro and by gene amplification in vivo.[2]

[1] Bertino, J. R., "Toward Selectivity in Cancer Chemotherapy: The Richard and Hinda Rosenthal Foundation Award Lecture," *Cancer Res.* 39:293-304 (1979). [2] Lu, Y., et al., "Biochemical and Molecular Properties of Cisplantin-Resistant A2780 Cells Grown in Folinic Acid," *J. Biol. Chem.* 283:4891-4894 (1988).

Pattern Difference Between The DNA of DNA Polymerase β From Normal and Cancer Tissues FIGS. 8-11 depict EcoRI digestion for Southern analyses of DNA polymerase β DNA from four types of human cancer.

FIG. 8 is a Southern analysis comparison of the DNA of DNA polymerase β DNA from a human colon carcinoma HCT8 cell lines sensitive (S), and resistant (D) to cisplatin, normal colon tissue (N) and colon carcinoma tissue from a patient (PK) that failed cisplatin and 5 fluorouracil chemotherapy. The lane PK pattern from the carcinoma cells includes a band at a 5.5 Kb not present in the normal tissue pattern.

FIG. 9 is a Southern analysis of the DNA of the DNA polymerase β from the cancer tissue of six human ovarian carcinoma patients. Patients DM, MD, TS, BD and DL) were treated with cisplatin in combination with 5 fluorouracil. Patient HS was treated with cisplatin in combination with cytoxane. The polymerase β DNA from all patients except DM lost a high molecular weight band (20Kb) upon development of resistance to chemotherapy. A low molecular weight band (5.5 Kb) was lost in 3 of the 6 drug resistant patients, i.e., patients DL, BD, and D. In FIG. 9, lane D pertains to a drug resistant ovarian cell line and lane S pertains to drug sensitive ovarian cell line.

The FIG. 10 Southern analysis shows that the DNA from the DNA polymerase β gene from tissue from four breast carcinoma patients BC1-BC4 is characterized by an additional band at 5.2 Kb and at 5.5 Kb as compared with normal tissue (NBT). Tissue from three of the four patients (BC$_{1-3}$) yielded an additional band at 5.5 Kb. The 5.2 Kb bands provide a marker to discriminate normal from neoplastic tissue. The D and S lanes relate to drug resistant and drug sensitive human breast tissues.

The FIG. 11 Southern analysis shows that the DNA of the DNA polymerase β gene from human leukemia cells resistant to cisplatin (DDP), VP-16 or MTX has additional bands at about 15 Kb as compared to the same gene from normal tissue(s) lane 5. These band changes provide markers for drug resistance in neoplastic cells, including human leukemia cells. A like band change is not observed in the case of cells resistant to ara-C.

The foregoing experiments utilized normal tissue and untreated tissue as standards representing drug sensitive cells. Cells obtained from a patient prior to treatment and stored provide an internal drug sensitive cell standard.

Normal and colon carcinoma tissues were obtained from five separate patients and analyzed by the methods previously described for their restriction enzyme fragment pattern for DNA polymerase α (FIG. 12a) and DNA polymerase β (FIG. 12b).

Figure 1:
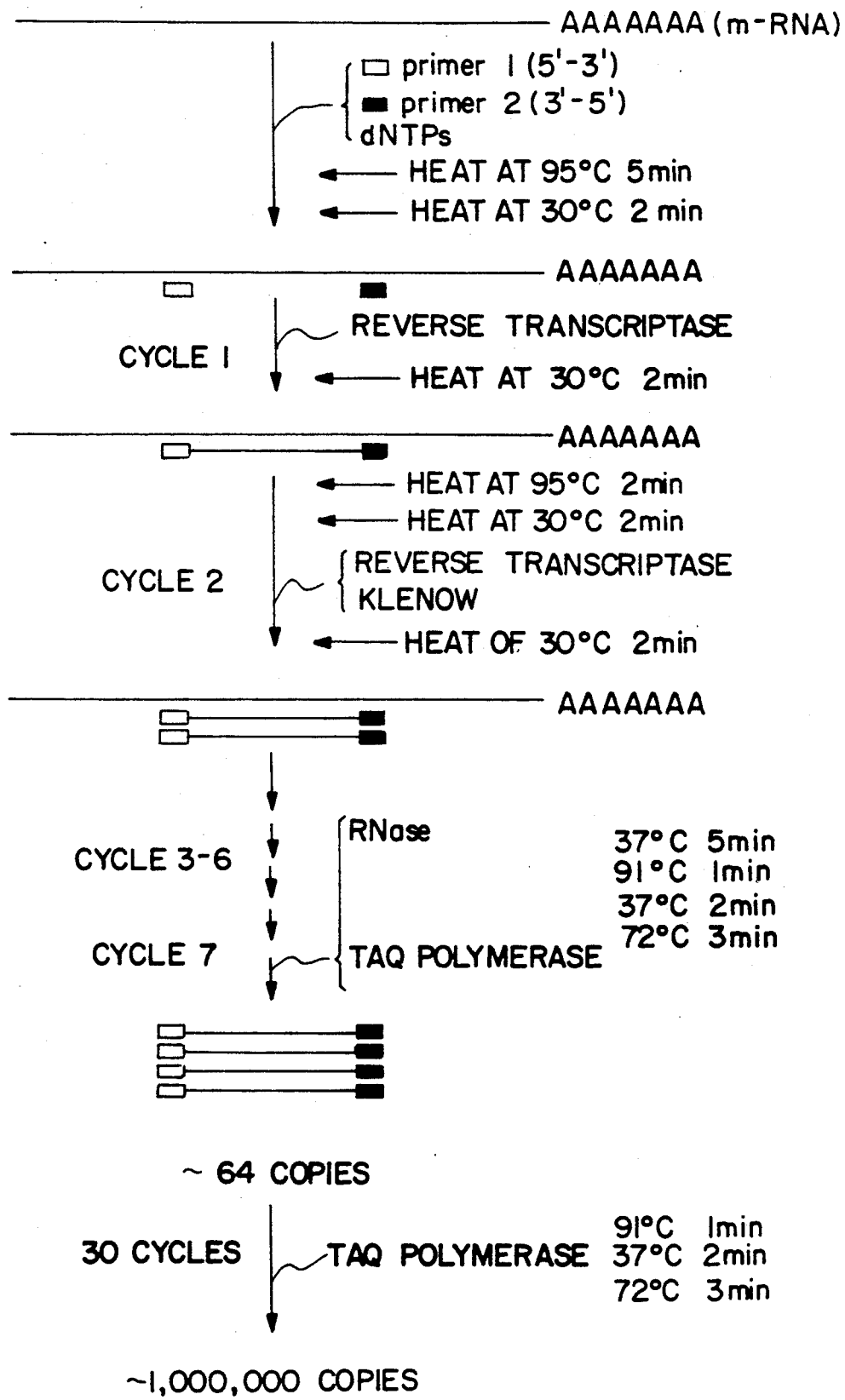

This invention includes visualization of temporal changes in the restriction enzyme fragment patterns and fragment pattern differences between normal, sensitive, and drug resistant tissue to monitor all stages of the progression of human tumor growth and of drug resistance.

Labelled nucleotide sequences in Southern or Northern analysis bands are routinely quantified by comparison of signal intensity from such bands with a standard. When the amount of the target sequence is quite small, such quantification techniques may be inadequate.

Pursuant to this invention the quantification of small DNA samples from tissue or cells is readily and efficiently accomplished.

The intensity of the signal from a labelled target sequence in a given Southern analysis band is a function of the number of rounds of amplification required to yield a band of preselected or predetermined signal intensity. See, e.g., *Kashani-Sabet, supra.*

This invention entails the determination of a set of standards which identify quantatively the signal intensity from a unique or preselected Southern analysis band after a selected number of PCR amplification rounds.

Comparison of the signal intensity of like Southern analysis bands derived from patient cell or tissue samples similarly amplified for a like number of rounds provides a ready and efficient monitor of the progress of both tumor size and tumor drug resistance.

EXAMPLE

Tissue or cell samples are prepared with known, progressively increasing quantities of a gene transcript which yields a unique cancer marker band. For example, colon carcinoma tissue or cell samples containing progressively increasing specific amounts of the transcript of DNA polymerase β are prepared. The DNA polymerase β target DNA sequence in each sample is PCR amplified under like conditions for each of a plurality of predetermined rounds. The intensity of the signal from each amplified sample after each predetermined plurality of rounds is recorded to provide a set of standards. Each standard in the set is the quantified intensity of the signal after one of the predetermined pluralities of amplification rounds.

DNA from a patient tissue cell sample is subjected to Southern analysis by the method used to prepare the standards. The intensity of the signal from the unique marker band after amplification for one or more of the pluralities of rounds used to prepare the standards is measured. Comparison of these signal intensity measurements from DNA of the patient sample with the standards provides a monitor of the existence and progress of tumor size and of tumor drug resistance of the patient samples.

The absence and continuing absence of a signal from the patient samples indicates freedom at least from the type of tumor to which the analyses apply. The initial appearance of a signal from a patient sample at a given amplification round level is evidence of incipient or appearing drug resistance. Increase in the magnitude of the signal in subsequently taken samples provides a temporal monitor of tumor progression per se and of tumor resistance to chemotherapy.

I claim:

1. A method for determining the presence or absence of cancer in a human patient which comprises:
   (i) selecting a human gene from the group consisting of the dihydrofolate reductase gene, the DNA polymerase beta gene, the dTMP synthase gene, the c-fos gene, the c-myc gene and the H-ras gene, the transcripts of which, if said patient has cancer, contain a DNA marker having a target DNA sequence which is not present in the transcripts from the same gene if said patient does not have cancer;
   (ii) analyzing the transcripts of said gene to determine the presence or absence of said DNA marker, said analysis comprising a determination of whether or not a probe complementary to said target sequence, when said patient has cancer, will hybridize to said target sequence.

2. A method for determining the presence or absence of cancer in a human patient which comprises:
   (i) selecting a human gene from the group consisting of the dihydrofolate reductase gene, the DNA polymerase beta gene, the dTMP synthase gene, the c-fos gene, the c-myc gene and the H-ras gene, the transcripts of which, if said patient has cancer, include a DNA marker having a target DNA sequence marker which is not present in the transcripts from the same gene if said patient does not have cancer;
   (ii) amplifying from a transcript from said gene a target DNA sequence which will include said DNA marker if present in said transcript; and
   (iii) analyzing said amplified target sequence to determine the presence or absence of said marker, said analysis comprising a determination of whether or not a probe complementary to said target cell sequence, when said patient has cancer, will hybridize to said target sequence.

3. A method as defined by claim 1 or claim 2 in which (i) said selected gene is the DNA polymerase $\beta$ gene; and
   (ii) said marker is a Southern analysis band at about 5.5 Kb.

4. A method as defined by claim 1, 2 or 3 for determining whether colon carcinoma, ovarian carcinoma, breast carcinoma or leukemia is present or absent in said patient.

5. A method as defined in claim 2 or 3 in which the target sequence is amplified by a polymerase chain reaction.

6. A method for determining whether human cancer cells are sensitive or resistanct to a drug which comprises:
   (i) selecting a human gene from the group consisting of the dihydrofolate reductase gene, the DNA polymerase beta gene, the dTMP synthase gene, the c-fos gene, the c-myc gene and the H-ras gene, the transcripts of which from sensitive and drug resistant cells contain uniquely different DNA or RNA sequences;
   (ii) analyzing the transcripts of said selected gene in a sample of said cancer cells to determine the presence or absence of a unique DNA sequence indicative of drug resistance.

7. A method for determining whether cancer cells are sensitive or resistant to a drug which comprises:
   (i) selecting a gene from the group consisting of the dihydrofolate reductase gene, the DNA polymerase beta gene, the dTMP synthase gene, the c-fos gene, the c-myc gene and the H-ras gene, the transcripts of which include DNA having a target DNA sequence when said cells are sensitive that is uniquely different when said cells are drug resistant;
   (ii) amplifying said target sequence present in a transcript of said selected gene;
   (iii) analyzing the amplified target sequence to determine the presence or absence of a DNA sequence indicative of drug resistance,
   wherein said analysis in step (iii) comprises a determination of whether or not a probe complementary to said target sequence when said cells are drug resistant will hybridize to said amplified target sequence.

8. A method as defined by claim 7 in which the analysis in step (iii) comprises a determination of whether or not a probe complementary to said target sequence when said cells are drug resistant will hybridize to said amplified target sequence.

9. A process as defined by claim 8 in which said selected cancer gene is the dTMP synthase gene and said probe includes the sequence AGG ATG TGT TGT GGA TCT GCC CA.

10. A process as defined by claim 8 which said selected gene is dihydrofolate reductase and said probe includes the sequence GTT CTG GGA CAC AGC GAC GAT GCA.

11. A process as defined by claim 8 in which said selected gene is DNA polymerase $\beta$ and said probe includes the sequence ACC AGG GAC TAG AGC CCT CTC CCA G.

12. A process as defined by claim 8 in which said selected cancer gene is c-myc and said probe includes the sequence GAC CAC CGA GGG GTC GAT GCA CTC T.

13. A process as defined by claim 8 in which said selected cancer gene is c-fos and said probe includes the sequence TGA GTG GTA GTA AGA GAG GCT ATC.

14. A process as defined by claim 8 in which said selected cancer gene is H-ras and said probe includes the sequence 5'-ACCTCTATAGTAGGGTCGTA-3'.

15. A method as defined by claim 7 in which the analysis in step (iii) is a Southern analysis.

16. A method as defined by claims 6 or 7 in which:
(i) said cells are colon or ovarian carcinoma cells;
(ii) said selected cancer gene is the DNA polymerase β gene;
(iii) said drug is cisplatin, methotrexate, etoposide or 1-β-D-arabinofuranosylcytosine; and
(iv) the indication of drug resistance is the presence of a gel electrophoresis band at about 5.5 Kb.

17. The method as defined by claims 6 or 7 in which:
(i) said cells are leukemia cells;
(ii) said selected cancer gene is DNA polymerase β;
(iii) said drug is cisplatin; and
(iv) the indication of drug resistance is the presence of a gel electrophoresis band at about 15 Kb.

18. A method for detecting the progression of a human tumor by analysis of a human tumor cell or tissue sample which comprises:
(i) selecting a gene from the group consisting of the dihydrofolate reductase gene, the DNA polymerase beta gene, the dTMP synthase gene, the c-fos gene, the c-myc gene and the H-ras gene, the transcript of which from cancer cells includes a DNA marker not present in the transcript of said gene from normal cells;
(ii) amplifying a target sequence of said selected gene present in said cell sample which target sequence includes said marker if present;
(iii) detecting and quantifying the DNA containing said market present in said amplification product, said detecting of said DNA containing said marker present in said amplification product being performed by determining whether or not a probe complementary to said target sequence will hybridize to said amplified target sequence.

19. A method for detecting the progression of human tumor growth or of the progression of human tumor drug resistance by analysis of a human tumor cell or tissue sample which comprises:
(i) selecting at least one gene from the group consisting of the dihydrofolate reductase gene, the DNA polymerase beta gene, the dTMP synthase gene, the c-fos gene, the c-myc gene and the H-ras gene, the transcript of which from drug resistant human cancer cells includes a DNA marker not present in drug sensitive cancer cells;
(ii) amplifying DNA from patient samples taken at a series of defined time intervals a target sequence of said selected gene present in said cell samples which target sequence includes said marker;
(iii) detecting and quantifying the DNA containing said marker in each of said amplification products;
(iv) comparing the quantification values obtained in step (iii) with standard values,
said detecting of said DNA containing said marker present in said amplification product being performed by determining whether or not a probe complementary to said target sequence will hybridize to said amplified target sequence.

20. A method as defined by claim 19 in which the amplification in step (ii) is accomplished by a polymerase chain reaction.

21. A method as defined by claim 19 in which the DNA is quantified in step (iii) by measuring the amplitude of the signal from labelled DNA in a particular Southern analysis band.

Figure 2:
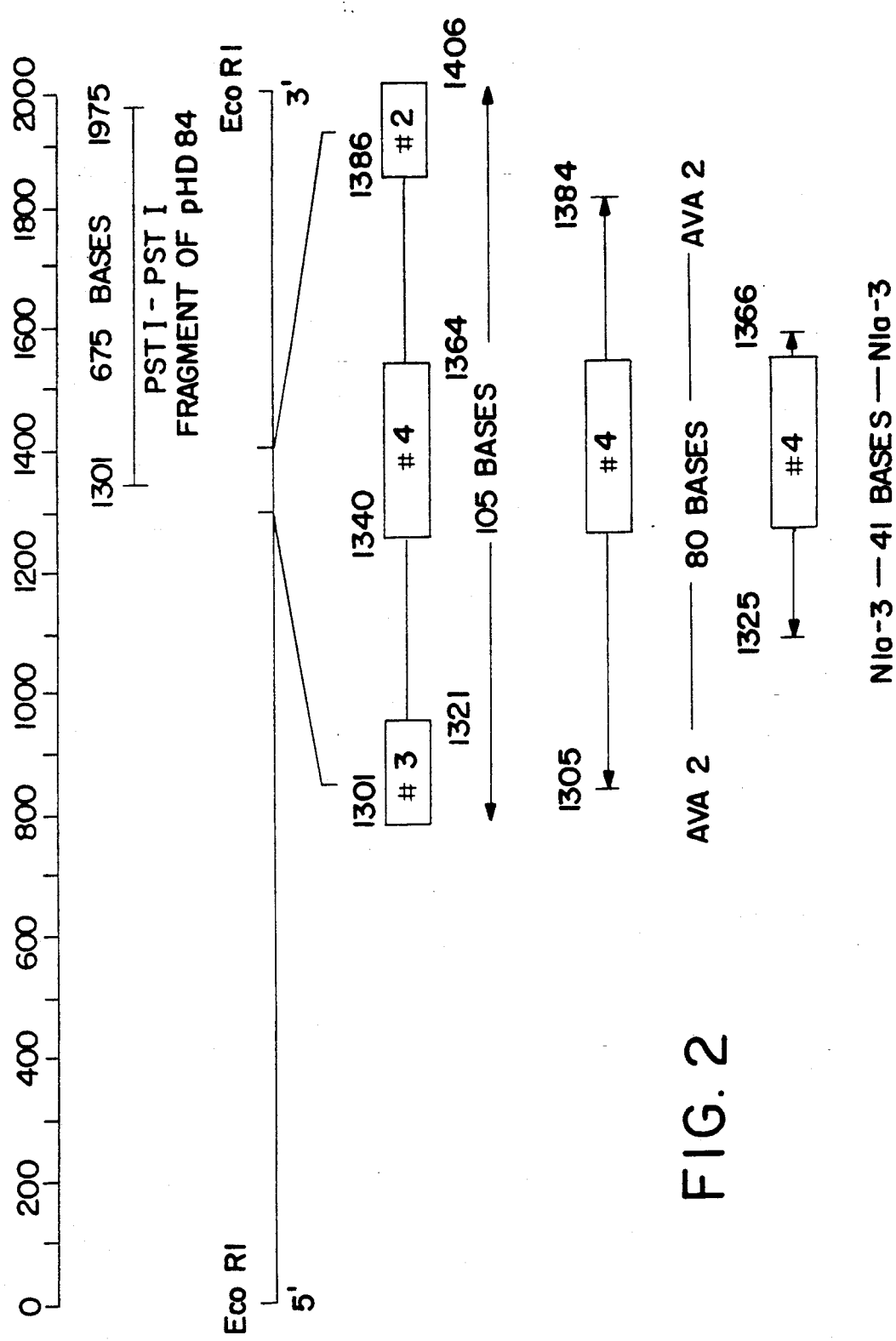

22. A method which comprises amplifying a human dihydrofolate reductase gene sequence by a polymerase chain reaction in which the primers utilized have the sequence of and are positioned as shown in FIG. 2.

Figure 3:
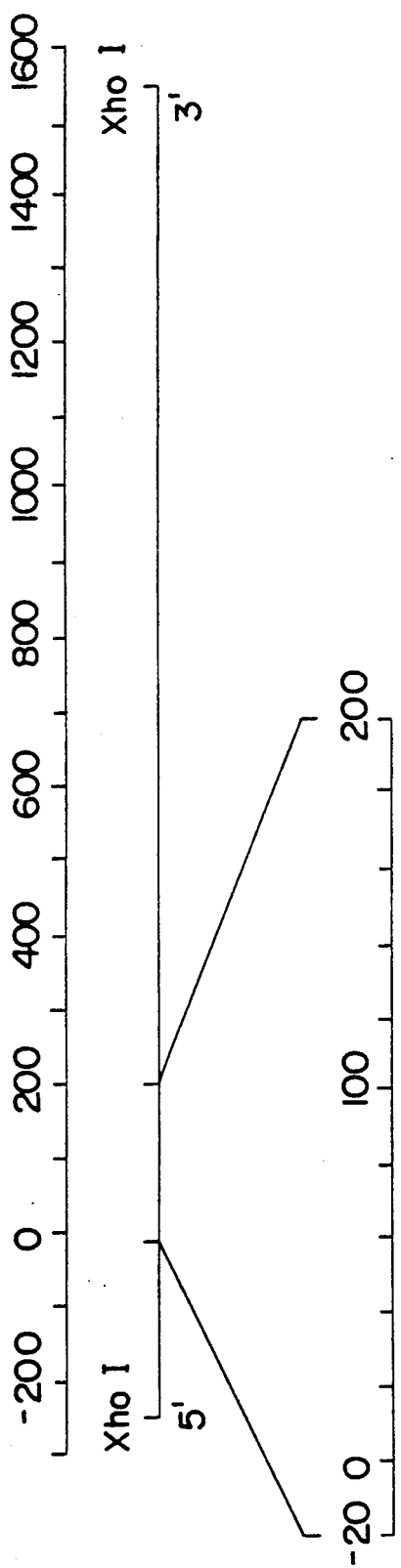

23. A method which comprises amplifying a dTMP synthase gene sequence by a polymerase chain reaction in which the primers utilized have the sequence of and are positioned as shown in FIG. 3.

Figure 4:
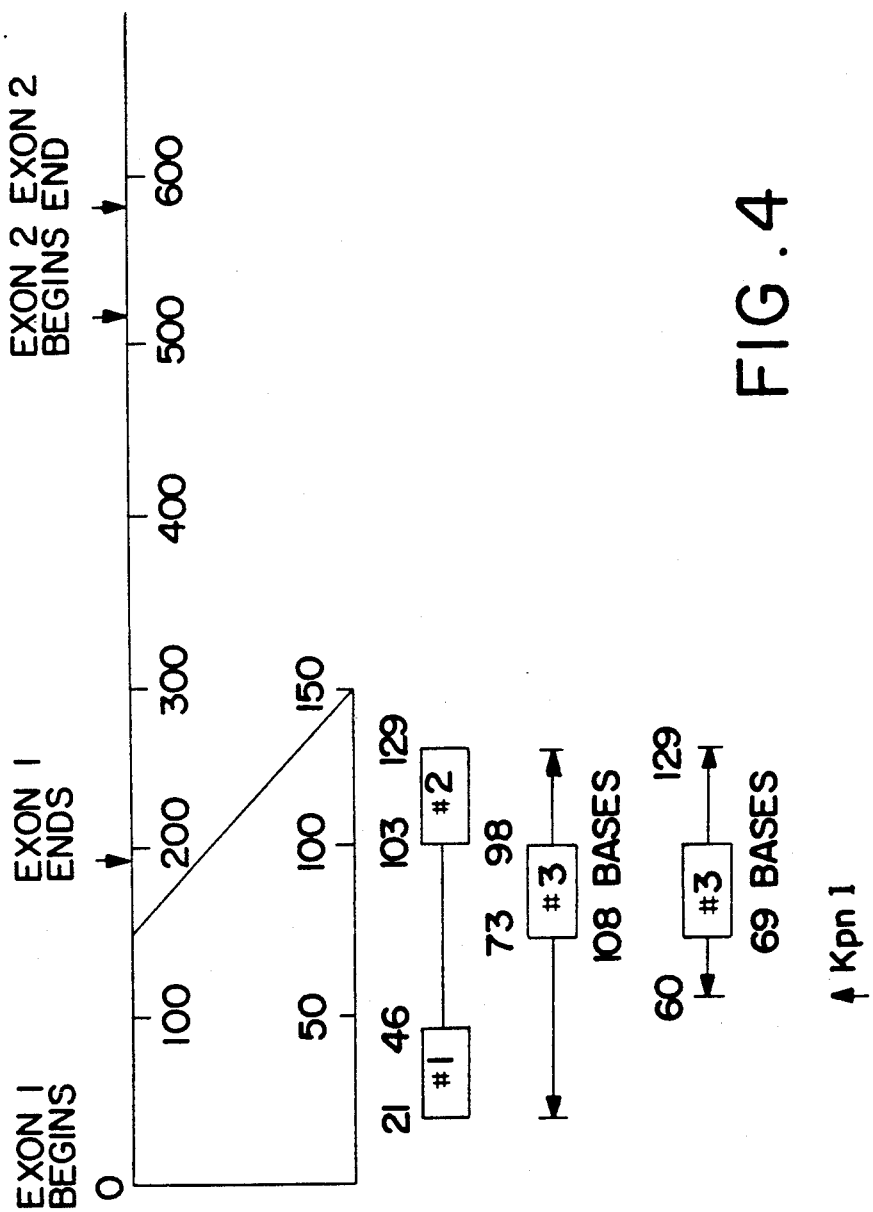

24. A method which comprises amplifying a DNA polymerase β gene sequence by a polymerase chain reaction in which the primers utilized have the sequence of and are positioned as shown in FIG. 4.

Figure 5:
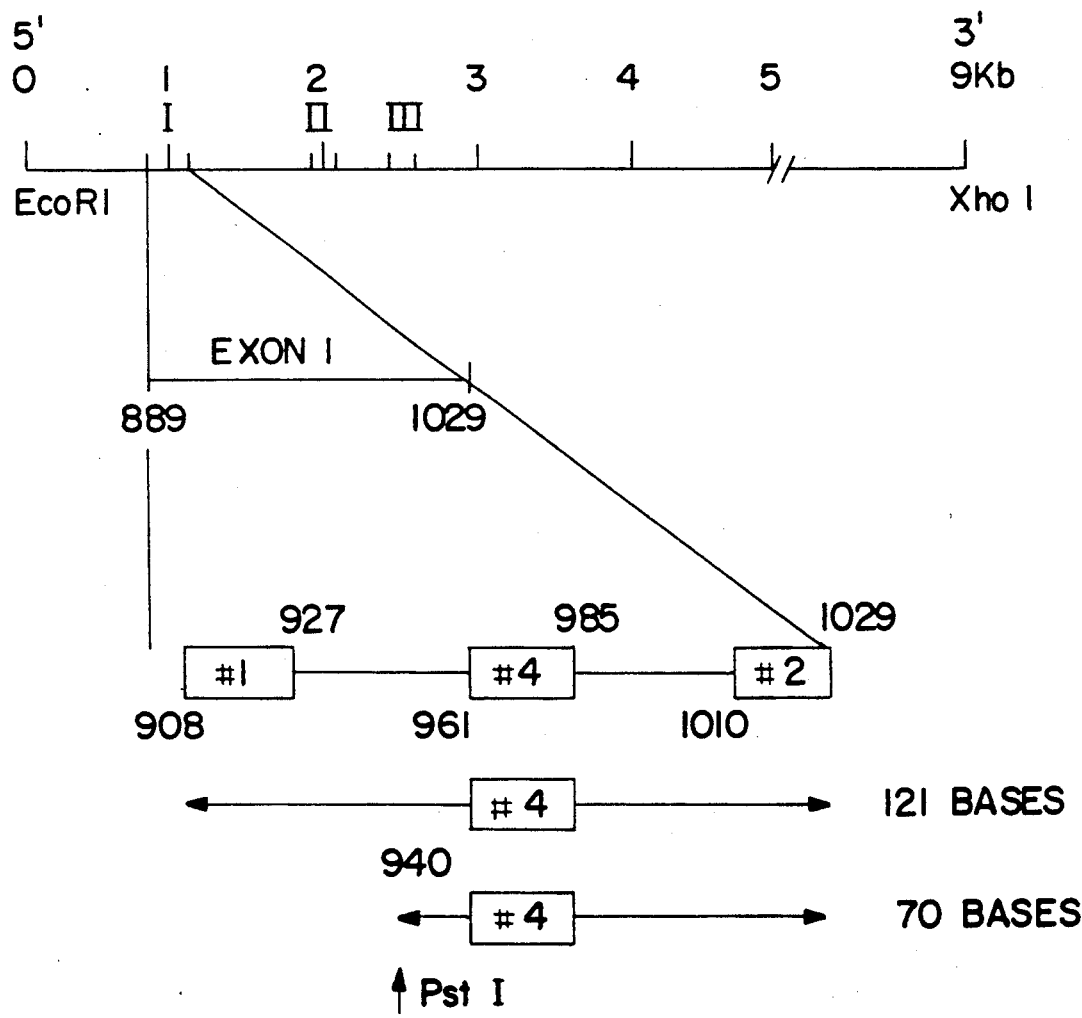

25. A method which comprises amplifying a c-fos gene sequence by a polymerase chain reaction in which the primers utilized have the sequence of and are positioned as shown in FIG. 5.

Figure 6:
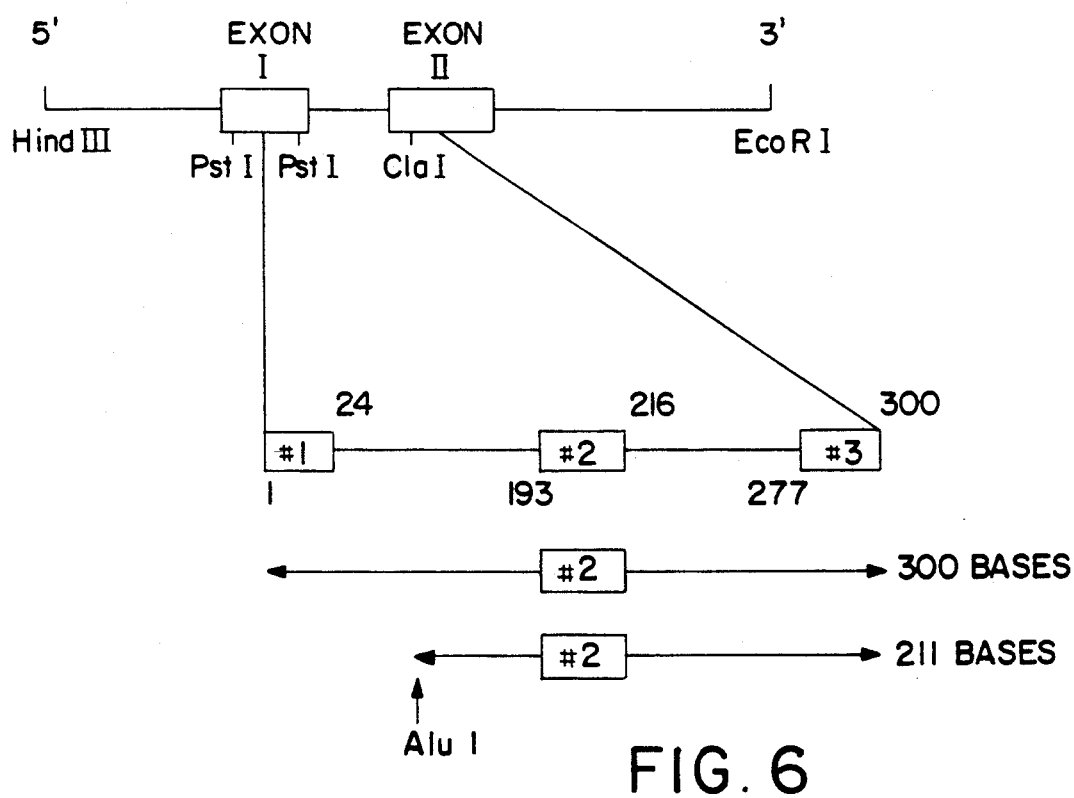

26. A method which comprises amplifying a c-myc gene sequence by a polymerase chain reaction in which the primers utilized have the sequence of and are positioned as shown in FIG. 6.

Figure 7:
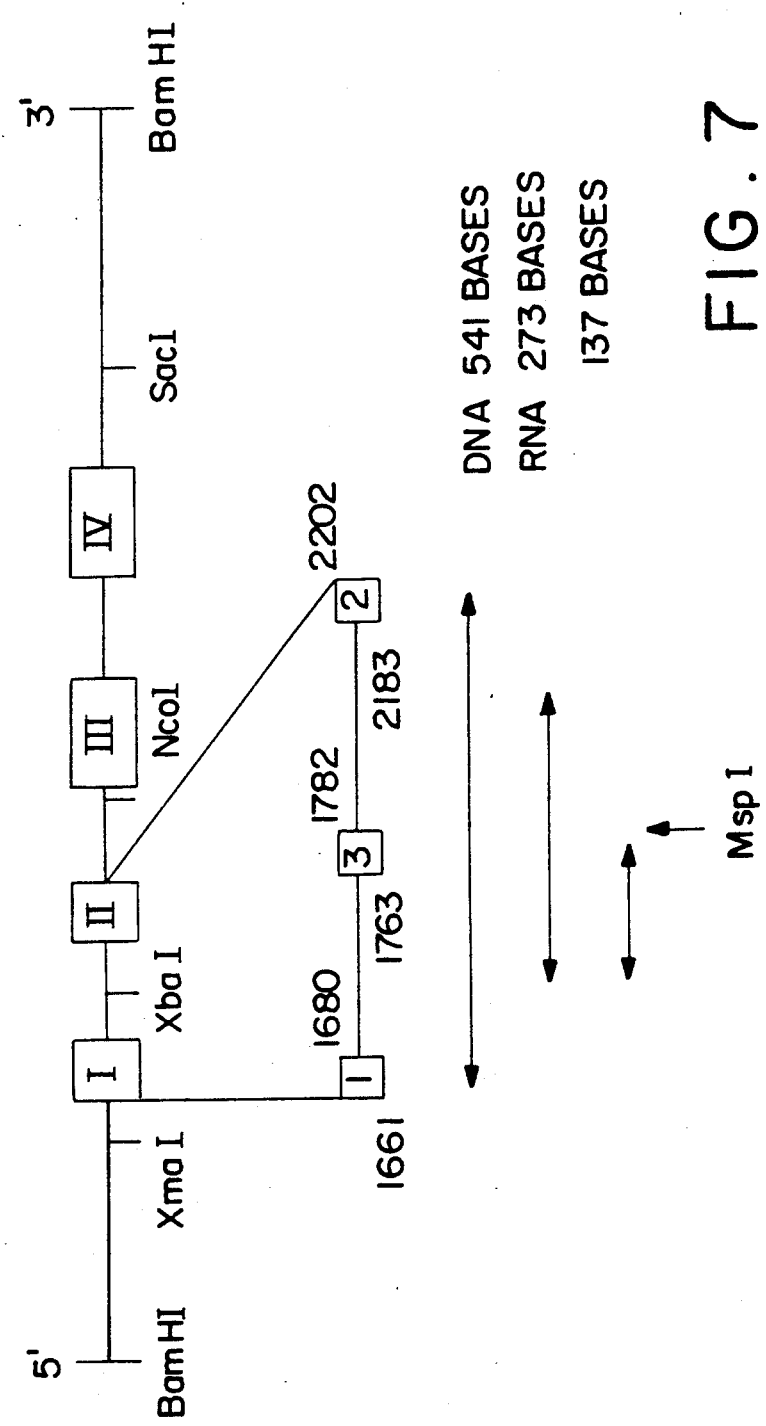
Figure 8:
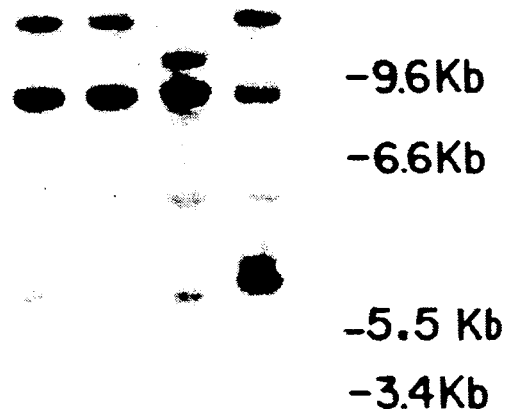
Figure 9:
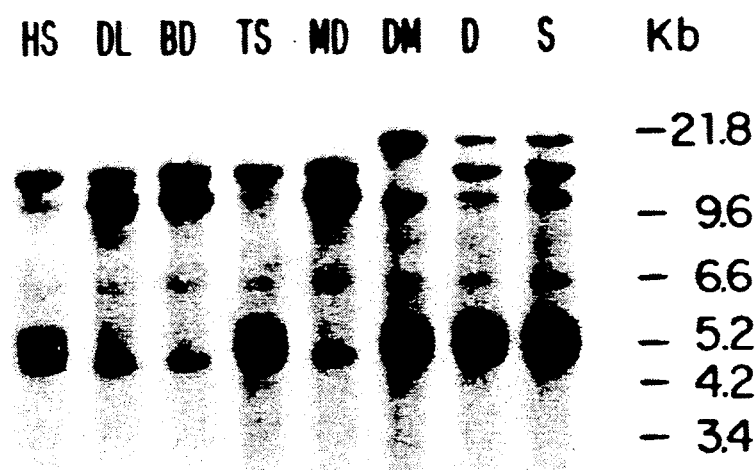
Figure 10:
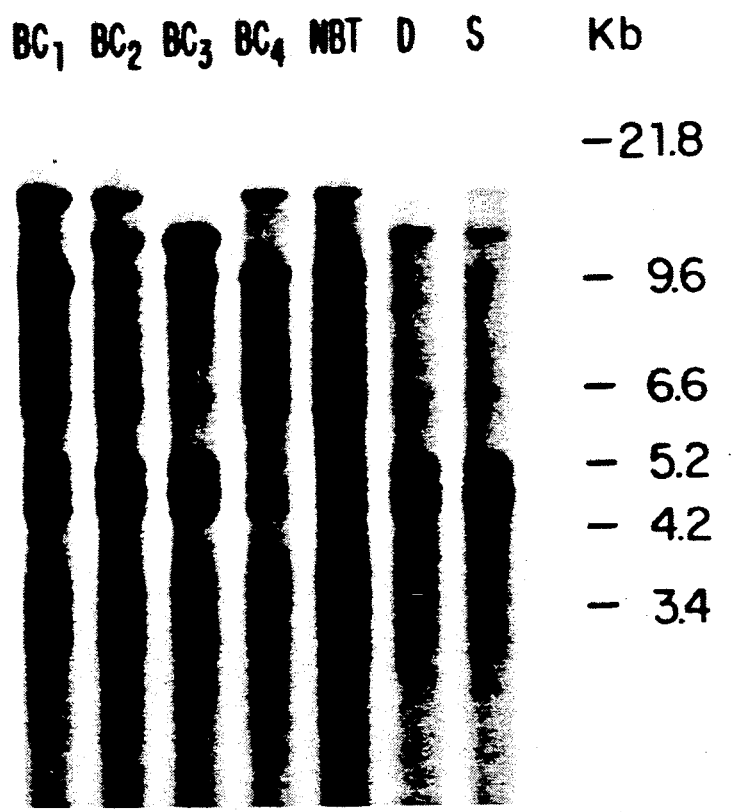
Figure 11:
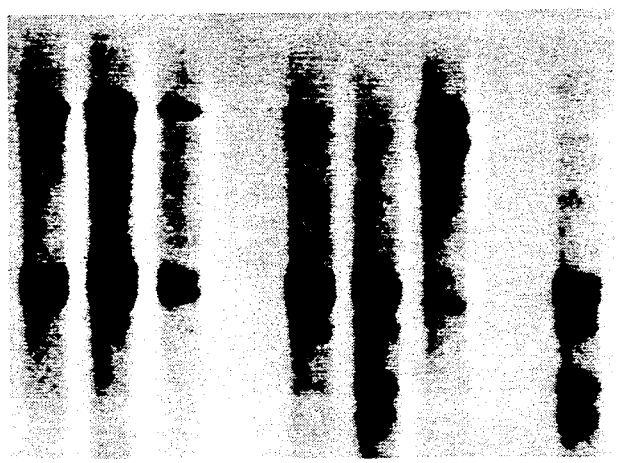
Figure 12A:
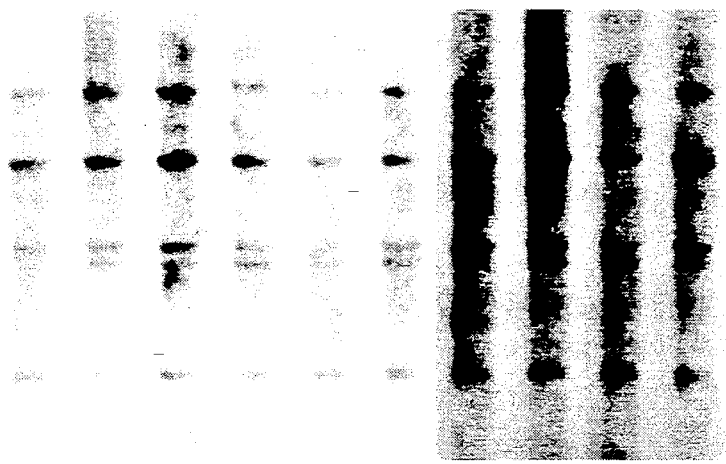
FIG. 12a shows by Southern analysis that the restriction enzyme pattern of the DNA from DNA polymerase α is similar for the normal (N 1-5) and colon carcinoma (T 1-5) samples.
Figure 12B:
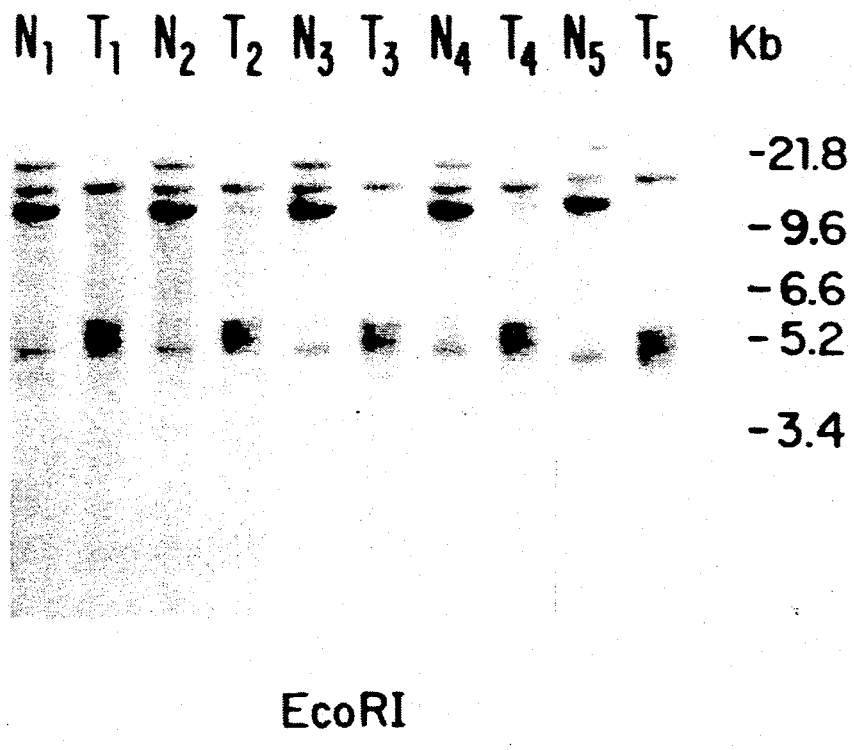
FIG. 12b, shows a Southern analysis of the restriction enzyme patterns of the DNA of DNA polymerase β, the tumor samples T1-T5 lack bands at 12 Kb and 15 Kb, present in the normal tissue samples (N 1-5). Two bands at 5.2 Kb and 5.5 Kb, not present in the normal tissue samples, are present in the colon cancer samples.

27. A method which comprises amplifying a H-ras gene sequence by a polymerase chain reaction in which the primers utilized have the sequence of and are positioned as shown in FIG. 7.

28. A synthetic oligonucleotide including the consisting essentially of a sequence selected from the group consisting of
(i) 5'-CGGAGGTCCTCCCGCTGCTGT-3';
(ii) 5'-GAGCGGTGGCCAGGGCAGGTC-3';
(iii) 5'-GTTCTGGGACACAGCGACGATGCA-3';
(iv) 5'-GCCATGCCTGTGGGCCGGCCTTCCCCGGAG-3';
(v) 5'-AGGGTGCCGGGGTTGCCCGTGCGGT-3';
(vii) 5'-GGAGCTGGGTTGCTCCTGCTCCCGT-3';
(viii) 5'-GCCTTCCGTTTGCTCATGGCGGCCT-3';
(ix) 5'-ACCAGGGACTAGAGCCCTCTCCCAG-3';
(x) 5-CTGCGCGTTGACAGGCGAGC-3';
(xi) 5-ACGCAGACTACGAGGCGTCA-3';
(xii) 5-TGAGTGGTAGTAAGAGAGGCTATC-3';
(xiii) 5-TCCAGCTTGTACCTGCAGGATCTG-3';
(xiv) 5-GACCACCGAGGGGTCGATGCACTCT-3';
(xv) 5'-AGGAGCCTGCCTCTTTTCCACAGA-3'.

* * * * *

UNITED STATES PATENT AND TRADEMARK OFFICE
CERTIFICATE OF CORRECTION

PATENT NO. : 5,085,983

DATED : February 4, 1992

INVENTOR(S) : Kevin J. Scanlon

It is certified that error appears in the above-identified patent and that said Letters Patent is hereby corrected as shown below:

Column 10, line 32, delete "including the".

Signed and Sealed this

Twenty-eighth Day of September, 1993

Attest:

BRUCE LEHMAN

Attesting Officer

Commissioner of Patents and Trademarks